United States Patent [19]
Kamahori et al.

[11] Patent Number: 4,823,168
[45] Date of Patent: Apr. 18, 1989

[54] FLOW-THROUGH CELL FOR A PHOTOMETER FORMED USING A PAIR OF CELL BODY MEMBERS

[75] Inventors: Masao Kamahori; Yoshio Watanabe; Junkichi Miura, all of Hitachi; Mamoru Taki, Ibaraki; Hiroyuki Miyagi, Mito, all of Japan

[73] Assignee: Hitachi, Ltd., Tokyo, Japan

[21] Appl. No.: 116,543

[22] Filed: Nov. 4, 1987

[30] Foreign Application Priority Data

Nov. 7, 1986 [JP] Japan .................................. 61-263783

[51] Int. Cl.⁴ ............................................. G01N 21/05
[52] U.S. Cl. ..................................... 356/246; 250/576
[58] Field of Search ....................... 356/246, 440, 410; 250/576

[56] References Cited

U.S. PATENT DOCUMENTS 3,751,173  8/1973  Sanz et al. .................... 356/243
4,575,424  3/1986  Allington et al. ............. 356/246 X
4,643,570  2/1987  Mächler et al. ................ 250/576 X

FOREIGN PATENT DOCUMENTS 0186755   7/1986  European Pat. Off. ............. 356/246
60-125540  7/1985  Japan .
60-235041 11/1985  Japan .

Primary Examiner—Vincent P. McGraw
Attorney, Agent, or Firm—Antonelli, Terry & Wands

[57] ABSTRACT

A flow cell for a photometer, which comprises a cell body integrated from a pair of cell body members by joining, at least one of which is provided with a linear groove on the joining surface of the cell body member from one end to another to the full length, as exposed to the joining surface, the groove playing both roles of a liquid sample passage and a detecting light path by the integration of the cell body members, and is further provided with a liquid sample inlet passage at a position near one end of the groove and a liquid sample outlet passage at a position near the other end of the groove, both passages being communicated with the grooves, the linear groove being provided with a light reflecting layer to the full length of the linear groove, and a pair of light transmission window members joined with the flow cell body at both ends on the groove-open sides thereof is provided, where polishing of the grooves is readily carried out and random reflection of light or absorption of light due to poor reflection is reduced, and the turbulent flow of a liquid sample and generation of noise are suppressed.

23 Claims, 5 Drawing Sheets

FLOW-THROUGH CELL FOR A PHOTOMETER FORMED USING A PAIR OF CELL BODY MEMBERS

BACKGROUND OF THE INVENTION

This invention relates to a flow cell for a photometer, and particularly to a flow cell for a photometer suitable for a liquid chromatographic detector.

A conventional flow cell for an optical detector comprises a plate-shaped, flow cell body provided with a light path perforation at the center and with a liquid sample inlet passage and a liquid sample outlet passage at both ends of the perforation, and a pair of window members joined at both sides of the plate-shaped, flow cell body, where the flow cell is made smaller in size and the diffusion of liquid sample bands is reduced, as disclosed in Japanese Patent Application Kokai (Laid-open) No. 60-125540.

In the conventional flow cell, no consideration is given to a method for forming the perforation and there is such a problem that a separation efficiency of column effluent components is lowered in the liquid chromatography due to the dead volume or disturbance in the liquid sample flow in the liquid sample flow passages and at joints between the liquid sample flow passages and the light path.

Japanese Patent Application Kokai (Laid-open) No. 60-235041 (=U.S. Pat. No. 4,643,570=European Patent Application No. 0158948) discloses a flow cell (cuvette) comprising two cuvette body halves, at least one of which is composed of a light-transmitting material, the cuvette halves having respective planar surfaces defining the interface between the body halves when the cuvette is assembled, and having recess means in the planar surfaces to define a measuring space as well as inlet and outlet channels communicating with the space. This conventional flow cell has a very small flow cell (cuvette) volume, e.g. a measuring volume of a few nl, a spherical recess having a depth of 3–10 μm at the center, whereas a light path diameter (diameter of the cross section for the measurement beam) of 1 to 3 mm, that is, a shorter light path length in contrast to the light path diameter. In other words, this conventional flow cell has a very low measurement effect.

To improve the measurement effect, the conventional flow cell also proposes to use the reflected light, but use of the reflected light leads to a noise increase, but there is no disclosure of noise reduction in this prior art literature.

SUMMARY OF THE INVENTION

An object of the present invention is to provide a flow cell of light transmission type for a photometer, where the unwanted disturbance in the liquid sample flow is thoroughly suppressed.

Another object of the present invention is to provide a flow cell of light transmission type for a photometer, where the dead volume or the unwanted disturbance in the liquid sample flow is reduced by forming a light path and liquid sample flow passages in appropriate shapes in the flow cell, finely polishing the inner surfaces of the light path and liquid sample flow passages, and particularly providing a light reflecting layer on the light path to the full length.

These objects can be attained by a flow cell for a photometer, which comprises a cell body integrated from a pair of cell body members by joining, at least one of which is provided with a linear groove on the joining surface of the cell body member from one end to another to the full length, as exposed to the bonding surface, the groove playing both roles of a liquid sample passage and a detecting light path by the integration of the cell body members, and is further provided with a liquid sample inlet passage at a position near one end of the groove and a liquid sample outlet passage at a position near the other end of the groove, both passages being communicated with the groove, and a pair of light transmission window members joined with the flow cell body at both ends on the groove-open sides thereof.

According to the present invention, the linear grooves can be provided on the joining surfaces of both cell body members from one end to the other to the full length, symmetrically to each other and exposed to the joining surfaces.

Furthermore, according to the present invention, a light reflecting layer is preferably provided on the surfaces of linear grooves to the full length.

In the present invention, the liquid sample inlet passage and the liquid sample outlet passage are preferably provided on at least one of the joining surfaces of cell body members, as exposed to the joining surface and communicated with the first linear groove.

Since the light path can be formed by forming a straight groove on at least one of the joining surfaces, as exposed to the joining surface, and joining the cell body members, the groove can be readily polished or a light reflecting layer can be readily formed on the groove before joining the cell body members. Thus, random light reflection on the flow cell inside or light absorption due to poor reflection can be reduced and also the disturbance in the liquid sample flow through the light path can be suppressed. Furthermore, fabrication of a flow cell itself can be readily made.

Furthermore, in the present invention, the liquid sample inlet passage and the liquid sample outlet passage can be likewise formed on at least one of the joining surfaces of cell body members, as exposed to the joining surface, and thus their shapes suitable for reducing the disturbance in the liquid sample flow through the light path can be readily and appropriately formed or their surfaces can be readily and finely polished.

PREFERRED EMBODIMENTS OF THE INVENTION

Figure 1:
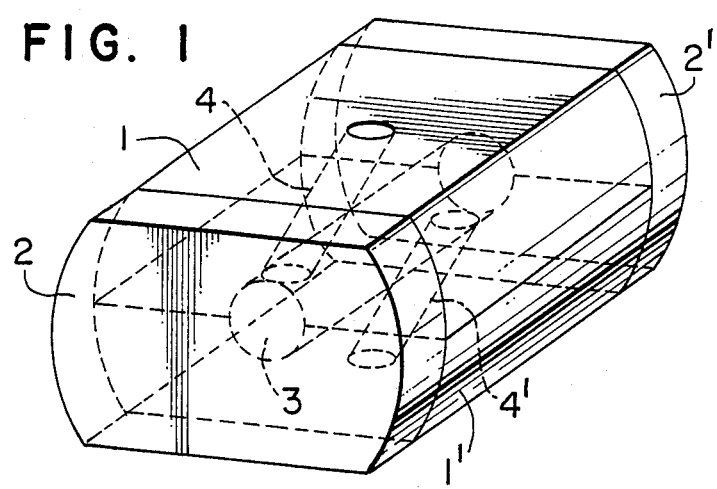
FIG. 1 is a schematic view of a flow cell according to one embodiment of the present invention.
Figure 2A:
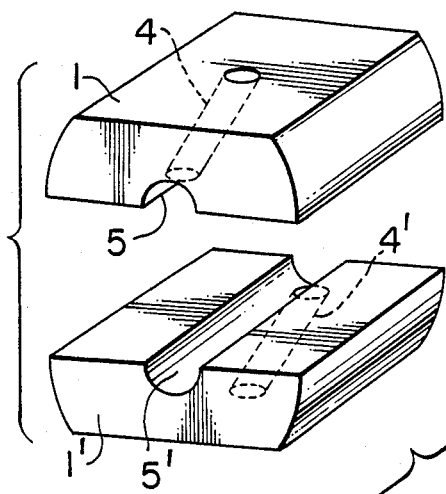
FIGS. 2A and 2B are schematic views showing assembling of the flow cell of FIG. 1.
Figure 2B:
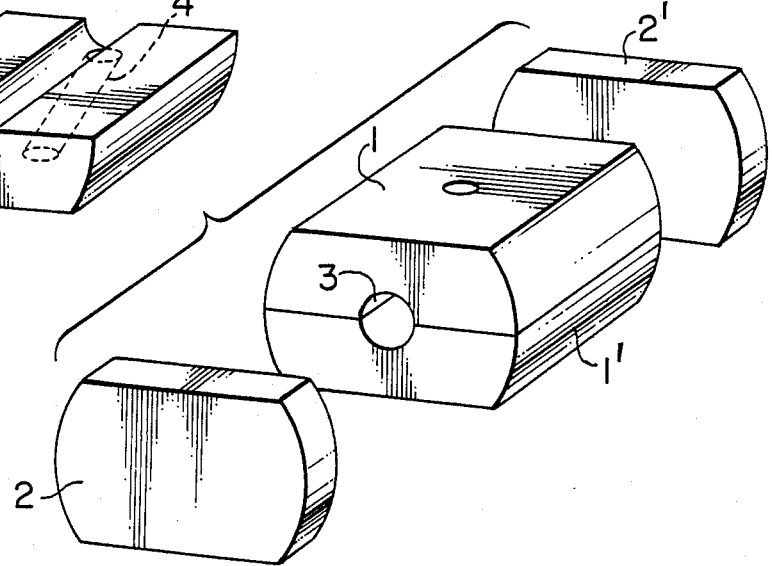

The present invention will be described in detail below, referring to FIGS. 1, 2A and 2B, showing the first embodiment of the present invention.

FIG. 1 shows an assembled flow cell for a photometer according to the present invention. The flow cell comprises a pair of cell body members 1 and 1' and light transmission window members 2 and 2' and has liquid sample inlet and outlet passages 4 and 4' and a light path 3 through which a liquid sample and a detecting light can pass.

FIGS. 2A and 2B are views showing assembling of the flow cell.

As shown in FIG. 2A, light path grooves 5 and 5' are formed on the joining surfaces of cell body members 1 and 1', respectively, and liquid sample inlet passage and outlet passage 4 and 4' are formed in the cell body members 1 and 1', respectively. The grooves 5 and 5' are formed by tightly joining and fixing a pair of the cell body members 1 and 1', and making a perforation along the joining surfaces at the center to the full length by a drill. After the formation of the perforation, the cell body members 1 and 1' are separated from each other, and the resulting linear grooves 5 and 5' on the respective joining faces are polished by lapping or chemical polishing. Then, the cell body members 1 and 1' are joined together by firm bonding, whereby a circular light path 3 is formed, as shown in FIG. 2B. The grooves 5 and 5' are formed by tightly joining and fixing the two cell body members 1 and 1' by drilling, the joining of the polished grooves 5 and 5' can be carried out with high precision only by aligning the contours of the cell body members 1 and 1'. Furthermore, liquid sample flow passages 4 and 4' are made by a drill. After the joining of the cell body members 1 and 1', light transmission window members 2 and 2' are joined to both ends of the flow cell, as shown in FIG. 2B.

In this embodiment, the cell body members 1 and 1' and the light transmission members 2 and 2' are composed of quartz glass. The cell body members 1 and 1' may be composed of other glass, e.g. soda glass, silicon, or silicon oxide. The joining surfaces of the cell body members 1 and 1' can be bonded together by melt bonding such as anodic bonding, or occasionally by smoothing the bonding surfaces and pressure bonding the joining surfaces, such as optical contact, to form a flow cell. No liquid leakage occurs at the joints of the bonding surfaces.

Another embodiment of the present invention will be described, referring to FIGS. 3, 4A and 4B.

Figure 3:
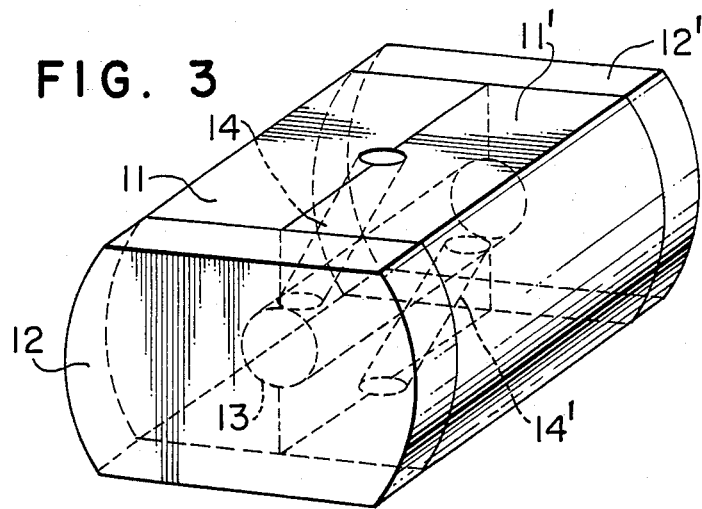
FIG. 3 is a schematic view of a flow cell according to another embodiment of the present invention.
Figure 4A:
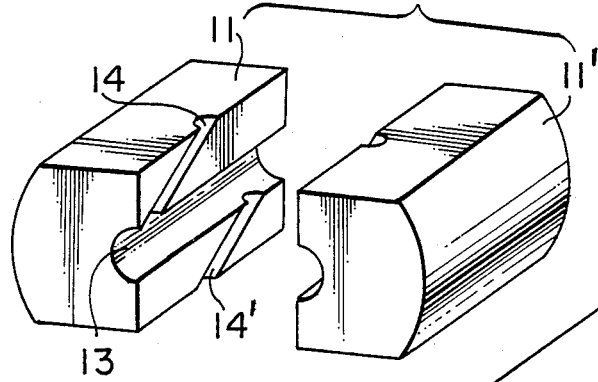
FIGS. 4A and 4B are schematic views showing assembling of the flow cell of FIG. 3.
Figure 4B:
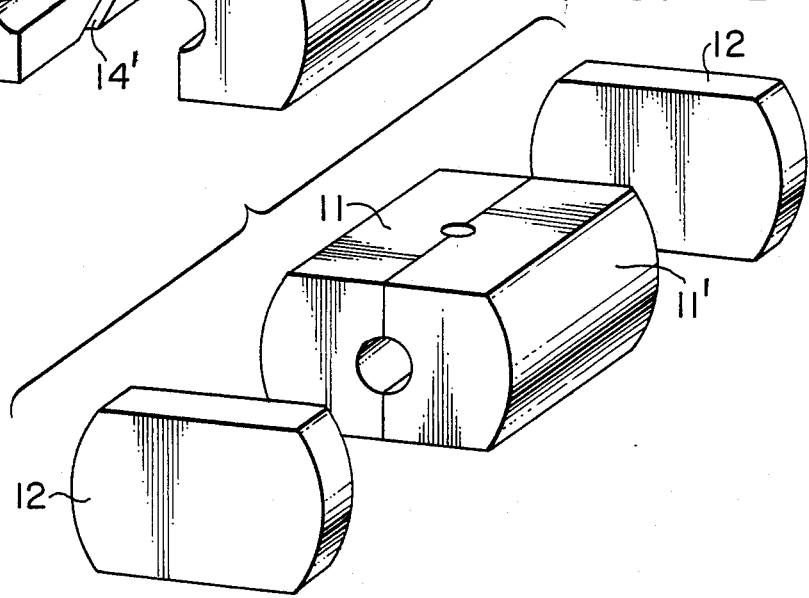

FIG. 3 shows an assembly of a flow cell for a photometer according to the present invention, where the flow cell comprises a pair of cell body members 11 and 11' and light transmission window members 12 and 12' and has liquid sample inlet passage 14 and outlet passage 14' and a light path through which a liquid sample and a detecting light pass. The structure of the flow cell is different from that of FIGS. 2A and 2B only in that the liquid sample inlet passage 14 and outlet passage 14' are formed on the respective joining surfaces of cell body members, as exposed to the joining surfaces and communicated with the straight light path grooves, as shown in FIGS. 4A and 4B.

Figure 5A:
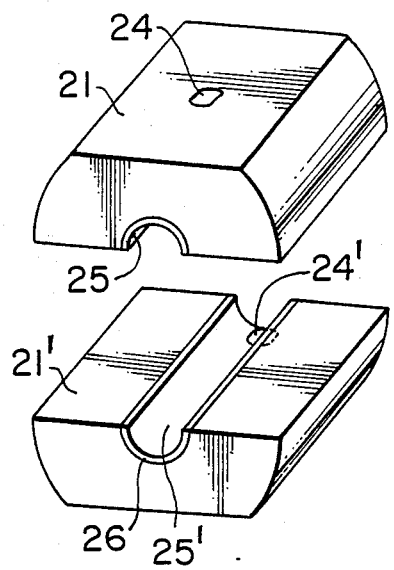
FIGS. 5A and 5B are schematic views showing assembling and cross-section of a flow cell according to other embodiment of the present invention.
Figure 5B:
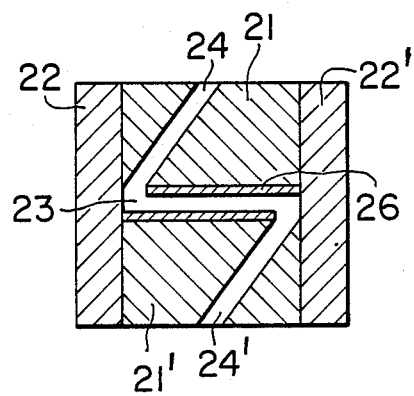

FIGS. 5A and 5B show a schematic view of assembling a flow cell having a light reflecting layer on the grooves and a cross-sectional view of the flow cell according to the present invention, respectively.

As shown in FIG. 5A, liquid sample inlet passage 24 and outlet passage 24' are provided on cell body members 21 and 21', respectively, as communicated with light path grooves 25 and 25', respectively, whereas the light path grooves 25 and 25' are formed on the joining surfaces of cell body members 21 and 21', respectively, as exposed to the joining surfaces. A light reflecting layer 26 is formed on the surfaces of the light path grooves 25 and 25'.

The light reflecting layer 26 can be formed on the grooves 25 and 25' by vacuum vapor deposition, by electron beam vapor deposition by allowing an electron beam to hit a sample in vacuum, thereby elevating the temperature of the sample and facilitating vapor deposition, or by sputtering by generating a plasma from an argon gas, sputtering a sample with the generated $Ar^+$, thereby physically scraping the sample. The light reflecting layer 26 is composed of a glass having a lower refractive index than that of the solvent in the liquid sample, or a metal of high reflectivity such as aluminum, rhodium, etc. In the case of aluminum light reflecting layer, the layer is coated with silicon oxide to give a corrosion resistance thereto.

After formation of the light reflecting layer 26 on the surfaces of the grooves 25 and 25', the cell body members 21 and 21' are joined together and light transmission window members 22 and 22' are bonded to both ends of cell body to form a flow cell, as shown in FIG. 5B.

The light reflecting layer can be likewise formed on the surfaces of grooves of embodiments of FIGS. 1 and 2A and 2B and FIGS. 3 and 4A and 4B.

The following Table shows noise test results of flow cells according to the present invention and a conventional flow cell whose light path was fabricated by drilling, as in, for example, said Japanese Patent Application Kokai (Laid-open) No. 60-125540. Tests were carried out under the following conditions:

Cell volume : 0.6 μl (inner diameter: 0.5 mm; light path length: 3 mm)

Detecting wavelength : 250 nm

Air or methanol was passed through the cell during the test. When methanol was passed through the cell, flow rate of methanol was 0.1 ml/min.

Random reflection due to the irregularities of flow cell inside surface or light absorption due to poor reflection appears by way of noises. As is evident from the following Table, noise could be reduced by polishing the inside surface, thereby reducing the irregularities of the flow cell inside surface. Furthermore, the noise was further reduced in a flow cell provided with a light reflecting layer on the light path inside surface by vacuum vapor depositing aluminum on the inside surface, and with a further $SiO_2$ layer thereon through electron beam vapor deposition, i.e. by allowing an electron beam to hit a $SiO_2$ sample, thereby elevating the temperature, thereby vacuum vapor deposition of $SiO_2$ onto the aluminum layer, to a total layer thickness of 2,000 Å, and thus the effect by the light reflecting layer is evident.

TABLE

| Flow cell | Noise (absolute) | |
|---|---|---|
| | Air through cell | Methanol through cell |
| Conventional (drill perforation type) | $5.0 \times 10^{-3}$ | $3.3 \times 10^{-3}$ |
| The invention (only inside polishing) | $3.0 \times 10^{-3}$ | $2.3 \times 10^{-3}$ |
| The invention (provision of light reflecting layer) | $1.0 \times 10^{-3}$ | $0.7 \times 10^{-3}$ |

Figure 6A:
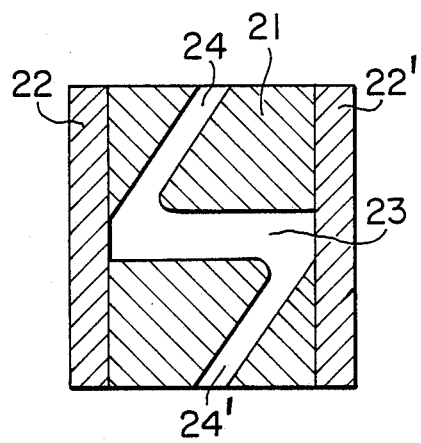
FIG. 6 are cross-sectional views showing groove shapes according to the present invention.
Figure 6B:
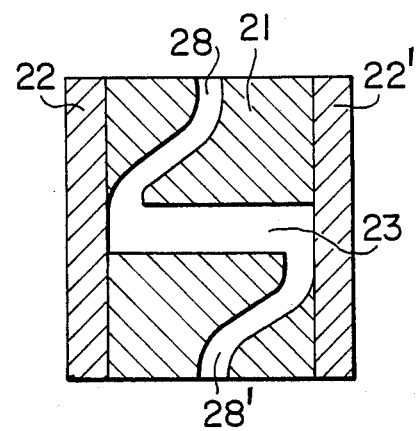

FIGS 6A and 6B are cross-sectional views of flow cells according to the present invention, where FIG. 6A shows that liquid sample inlet passage 24 and outlet passage 24', and a light path 23 are rounded at their joints, and FIG. 6B shows that liquid sample inlet passage 28 and outlet passage 28' are in a S shape. According to the rounded joints and rounded shapes of the liquid sample inlet and outlet passages, diffusion of liquid sample bands can have been made lower in the flow cell for the first time. Cell body members 21 and light transmission window members 22 and 22' are the same as used in the embodiment of FIG. 5.

Figure 7:
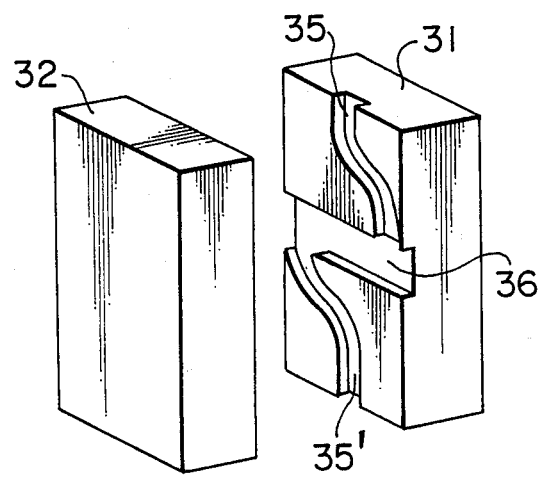
FIG. 7 is a schematic view of cell body members to be assembled according to further embodiment of the present invention.

Further embodiment of the present flow cell is shown in FIG. 7 by way of its assembling, where a light path groove 36 and S-shaped liquid sample inlet passage 35 and outlet passage 35' are formed only on the joining surface of a cell body member 31 composed of quartz glass. Then, the cell body member 31 is joined with another cell body member 32 without any groove thereon, and a pair of light transmission window members (not shown in the drawing) are bonded to both ends of the flow cell body at the groove-open sides to form a flow cell having a light path 36 and liquid sample inlet passage 35 and outlet passage 35'.

Figure 8A:
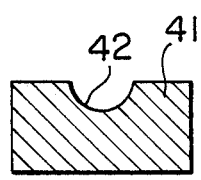
FIGS. 8A, 8B and 8C are cross-sectional views of grooves to be employed in the present invention.
Figure 8B:
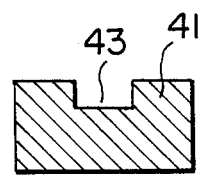
Figure 8C:
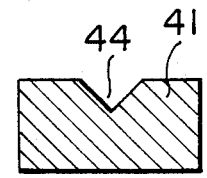

FIGS. 8A, 8B and 8C show cross-sectional views of light path grooves and liquid sample passage of various shapes. FIG. 8A shows a half-circle groove 42, FIG. 8B a square groove 43 and FIG. 8C a triangular groove 44, each on a cell body member 41. A groove of any other shape can be also used.

Figure 9:
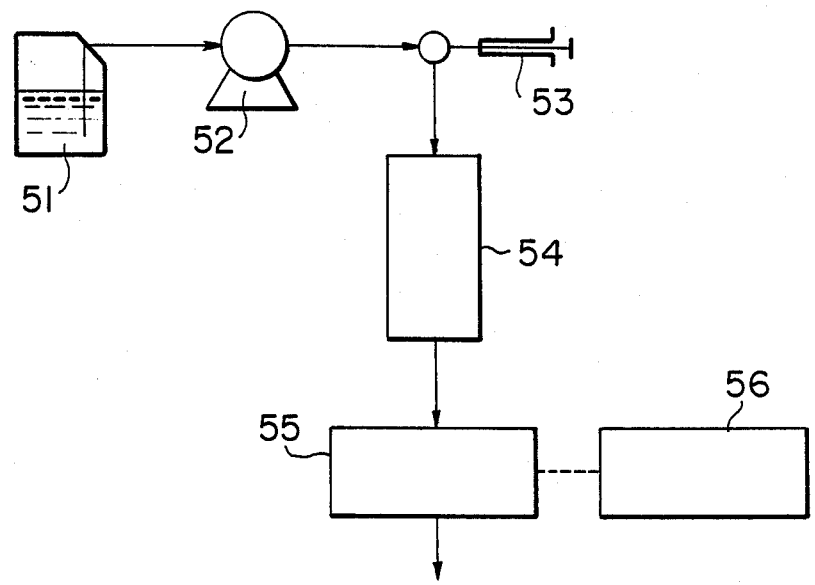
FIG. 9 shows a basic structure of a liquid chromatography using a flow cell of the present invention.

One example of a liquid chromatography using the present flow cell is shown in FIG. 9, where a liquid chromatograph comprises an eluting solution tank 51 for storing an eluting solution as a carrier, a pump for feeding the eluting solution from the tank 51, a sample injector 53 for introducing a mixed sample into the eluting solution, a separation column 54 for separating sample components as introduced, a spectrophotometer for detecting the sample components separated in the column 54 and a recorder 56 for recording output from the spectrophotometer 55.

Figure 10:
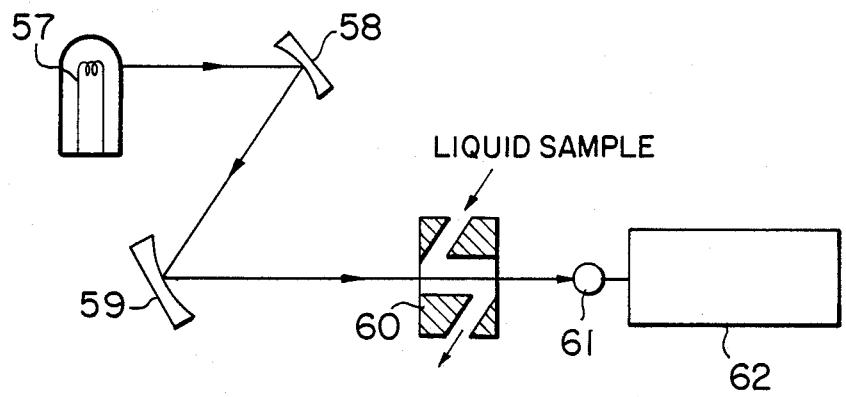
FIG. 10 shows a structure of a spectrophotometer using a flow cell of the present invention.

The spectrophotometer 55 is shown in FIG. 10, and comprises a light source 57, a light-collecting mirror 58 for collecting the light emitted from the light source 57, a diffraction lattice 59 for spectrolyzing the light collected on the mirror 58, a flow cell 60 through which the eluate from the separation column 54 as a liquid sample passes and also the spectrolyzed beam from the diffraction lattice 59 passes straight, a photodiode 61 for detecting the light that has passed through the flow cell 60 and a detection circuit 62 for converting the output from the photodiode 61 to a voltage.

According to the foregoing embodiments, the inside surfaces of the light path and liquid sample passages can be readily polished and thus the dead volume or disturbance in the liquid sample flow through the flow cell can be suppressed.

Furthermore, owing to easy polishing of the inside surfaces of the light path and liquid sample passages, random light reflection or light absorption on the inside surface of light path in the flow cell can be reduced and thus a high measurement effect can be obtained.

Still furthermore, owing to formation of a light reflecting layer, a flow cell intensively utilizing light reflection on the inside surface of light path can be effectively provided.

In the present flow cell of light transmission type, generation of noises due to uneven light absorption on the inside surface of light path can be reduced in spite of a rather longer light path.

What is claimed is:

1. A flow cell for a photometer, which comprises a cell body integrated from a pair of cell body members by joining, at least one of which is provided with a linear groove on the joining surface of the cell body member from one end to another to the full length, as exposed to the joining surface, the groove playing both roles of a liquid sample passage and a detecting light path by the integration of the cell body members, and is further provided with a liquid sample inlet passage at a position near one end of the groove and a liquid sample outlet passage at a position near the other end of the groove, both passages being communicated with the groove, the cell body members being formed of a material selected from the group consisting of glass, silicon and silicon oxide, and a pair of light transmission window members joined with the flow cell body at both ends of the groove-open sides thereof.

2. A flow cell for a photometer according to claim 1, wherein the liquid sample inlet passage and the liquid sample outlet passage are provided as grooves on the joining surface of the cell body member, as exposed to the joining surface and communicated with the first linear groove.

3. A flow cell for a photometer according to claim 2, wherein the liquid sample inlet passage and the liquid sample outlet passage are communicated with the first linear grooves at round corners.

4. A flow cell for a photometer according to claim 2, wherein the liquid sample inlet passage and the liquid sample outlet passage are in a S shape.

5. A flow cell for a photometer according to claim 1, wherein said linear grooves are grooves provided by fixing a pair of body members together and drilling through at least one of the body members to form grooves, and then polishing the grooves, so as to form the linear grooves of the cell body members.

6. A flow cell for a photometer according to claim 1, wherein the cell body members and light transmission window members are made of the same material.

7. A flow cell for a photometer according to claim 1, wherein the pair of cell body members are joined by bonding.

8. A flow cell for a photometer according to claim 7, wherein the bonding is a melt bonding or pressure bonding.

9. A flow cell for a photometer according to claim 1, wherein the liquid sample passage and detecting light path have a cross-sectional shape of a circle.

10. A flow cell for a photometer, which comprises a cell body integrated from a pair of cell body members by joining, both of which are provided with linear grooves symmetrically to each other on the joining surfaces of the cell body members from one end to another to the full length, as exposed to the joining surfaces, the grooves playing both roles of a liquid sample passage and a detecting light path by the integration of the cell body members, and at least one of which is further provided with a liquid sample inlet passage at a position near one end of the groove and a liquid sample outlet passage at a position near the other end of the groove, both passages being communicated with the groove, the cell body members being formed of a material selected from the group consisting of glass, silicon and silicon oxide, and a pair of light transmission window members joined with the flow cell body at both ends on the groove-open sides thereof.

11. A flow cell for a photometer according to claim 10, wherein the liquid sample inlet passage and the liquid sample outlet passage are provided as grooves symmetrically to each other on the joining surfaces of both cell body members, as exposed to the joining surfaces and communicated with the first linear grooves.

12. A flow cell for a photometer according to claim 11, wherein the liquid sample inlet passage and the liquid sample outlet passage are communicated with the first linear grooves at round corners.

13. A flow cell for a photometer according to claim 11, wherein the liquid sample inlet passage and the liquid sample outlet passage are in a S shape.

14. A flow cell for a photometer, which comprises a cell body integrated from a pair of cell body members by joining, at least one of which is provided with a linear groove on the joining surface of the cell body member from one end to another to the full length, as exposed to the joining surface, the groove playing both roles of a liquid sample passage and a detecting light path by the integration of the cell body members, and is further provided with a liquid sample inlet passage at a position near one end of the groove and a liquid sample outlet passage at a position near the other end of the groove, both passages being communicated with the groove, the cell body members being made of a material selected from the group consisting of glass, silicon and silicon oxide, the linear groove being provided with a light reflecting layer to the full length of the linear groove, and a pair of light transmission window members joined with the flow cell body at both ends on the groove-open sides thereof.

15. A flow cell for a photometer according to claim 14, wherein the liquid sample inlet passage and the liquid sample outlet passage are provided as grooves on the joining surface of the cell body member, as exposed to the joining surface and communicated with the first linear groove.

16. A flow cell for a photometer according to claim 14, wherein the liquid sample inlet passage and the liquid sample outlet passage are communicated with the first linear grooves at round corners.

17. A flow cell for a photometer according to claim 14, wherein the liquid sample inlet passage and the liquid sample outlet passage are in a S shape.

18. A flow cell for a photometer according to claim 14, wherein the photometer is adapted to have a liquid sample pass therethrough, the liquid sample including a solvent, and wherein said light reflecting layer is composed of a glass having a lower refractive index than that of the solvent of the liquid sample.

19. A flow cell for a photometer according to claim 14, wherein the light reflecting layer is made of aluminum, and has a coating of silicon oxide thereon.

20. A flow cell for a photometer, which comprises a cell body integrated from a pair of cell body members by joining, both of which are provided with linear grooves symmetrically to each other on the joining surfaces of the cell body members from one end to another to the full length, as exposed to the joining surfaces, the groove playing both roles of a liquid sample passage and a detecting light path by the integration of the cell body members, and at least one of which is further provided with a liquid sample inlet passage at a position near one end of the groove and a liquid sample outlet passage at a position near the other end of the groove, both passages being communicated with the groove, the cell body members being made of a material selected from the group consisting of glass, silicon and silicon oxide, the linear grooves being provided with a light reflecting layer to the full length of the linear grooves, and a pair of light transmission window members joined with the flow cell body at both ends on the groove open sides thereof.

21. A flow cell for a photometer according to claim 20, wherein the liquid sample inlet passage and the liquid sample outlet passage are provided as grooves symmetrically to each other on the joining of both cell body members, as exposed to the joining surfaces and communicated with the first linear grooves.

22. A flow cell for a photometer according to claim 21, wherein the liquid sample inlet passage and the liquid sample outlet passage are communicated with the first linear grooves at round corners.

23. A flow cell for a photometer according to claim 21, wherein the liquid sample inlet passage and the liquid sample outlet passage are in a S shape.

* * * * *